United States Patent [19]

Koenig et al.

[11] Patent Number: 5,041,086

[45] Date of Patent: Aug. 20, 1991

[54] CLINICAL CONFIGURATION OF MULTIMODE MEDICATION INFUSION SYSTEM

[75] Inventors: Paul A. Koenig, Valencia; John B. Slate, Studio City; O. Rey Rule, III, Santa Monica; Fredric C. Colman, Bel Air, all of Calif.

[73] Assignee: Pacesetter Infusion, Ltd., Sylmar, Calif.

[21] Appl. No.: 128,966

[22] Filed: Dec. 4, 1987

[51] Int. Cl.$^5$ .............................................. A61M 31/00
[52] U.S. Cl. ............................... 604/65; 128/DIG. 13
[58] Field of Search ............................. 604/65, 66, 67; 128/DIG. 12, DIG. 13

[56] References Cited

U.S. PATENT DOCUMENTS

| | | | |
|---|---|---|---|
| 4,525,163 | 6/1985 | Slavik et al. | 604/65 |
| 4,529,401 | 7/1985 | Leslie et al. | 128/DIG. 12 |
| 4,685,903 | 8/1987 | Cable et al. | 128/DIG. 12 |
| 4,692,145 | 9/1987 | Weyant | 604/65 |
| 4,710,166 | 12/1987 | Thompson et al. | 604/65 X |
| 4,731,051 | 3/1988 | Fischell | 604/67 |
| 4,756,706 | 7/1988 | Kerns et al. | 604/66 |

*Primary Examiner*—Kyle L. Howell
*Assistant Examiner*—J. P. Lacyk
*Attorney, Agent, or Firm*—Leslie S. Miller

[57] ABSTRACT

A medication infusion system may be selectively configured to perform an emulation of any one of a plurality of Device Types corresponding to the environment of use. The particular parameters which relate to a given Device Type are set into the system either at the factory or by biomedical engineers at the hospital or other medical institution by resort to an intercoupled computer driven by appropriate software. With the system set up in this fashion, a clinical user can select a given Device Type and can view but cannot change the critical operating parameters thereof. Substantial economies and improvement of device operation are realized by the provision of one switchable system in place of the plurality of different types of devices now required in a given institution.

30 Claims, 2 Drawing Sheets

CLINICAL CONFIGURATION OF MULTIMODE MEDICATION INFUSION SYSTEM

IDENTIFICATION OF RELATED PATENT APPLICATIONS

This application is related to nine other co-pending patent applications. These patent applications are U.S. Serial No. 127,33, entitled "Disposable Cassette for a Medication Infusion System," U.S Ser. No. 127,350, entitled "Piston Cap and Boot Seal for a Medication Infusion System," U.S. Ser. No. 128,122, entitled "Pressure Diaphragm for a Medication Infusion System," U.S. Ser. No. 128,009, entitled "Cassette Optical Identification Apparatus for a Medication Infusion System," U.S. Ser. No. 128,121, entitled "Air-In-Line Detector for Medication Infusion System," U.S. Ser. No. 127,359, entitled "Cassett Loading and Latching Apparatus for a Medication Infusion System," U.S Ser. No. 127,133, entitled "Mechanical Drive System for a Medication Infusion System," all of which were filed Dec. 1, 1987, and U.S Ser. No. 128,133, entitled "Fluid Delivery Control and Monitoring Apparatus for a Medication Infusion System," and U.S. Ser. No. 128,978, entitled "User Interface for Multimode Medication Infusion System," filed concurrently herewith. All of these applications are assigned to the assignee of this application.

BACKGROUND OF THE INVENTION

The present invention relates generally to systems for continuously infusing medication into a patient and, more particularly, to apparatus for the configuration of such a system for automatic operation in a selected mode.

Until recently there were two major techniques available for delivering drugs to a patient when the drugs cannot be orally administered. The first technique is to inject the drug into the patient with a syringe and needle to deliver an appreciable dose at relatively infrequent intervals. This technique is not always satisfactory, particularly when the drug being injected is potentially lethal, possibly has undesirable side effects when given in a large dosage, or must be delivered more or less continuously to arrive at a desired therapeutic result. This technique leaves much to be desired. The risks of overdosage or harmful side effects may be reduced by giving smaller injections at more frequent intervals, an inconvenient and not altogether satisfactory alternative.

The need for delivering a drug more or less continuously to achieve a desired therapeutic effect gives rise to the second technique, which involves a continuous delivery of medication to the patient, typically through an intravenous drip. Medication may also be administered using an intravenous system with an injection into a complicated and cumbersome interconnection of Iv tubes, hoses, and other components. Drop counters are used to measure the amount of fluid delivered, and medications are often delivered in a large dose through injection into the Iv lines, with the medication being somewhat dilute by the fluid.

A relatively recent alternative to these two techniques of administering medication to a patient is the medication infusion pump. A valuable and much needed development, the medication infusion pump can be used to administer drugs to a patient in small, carefully measured doses at frequent intervals or, with some devices, slowly but uninterruptedly. A therapeutic regimen with an infusion pump can be controlled electronically to administer precisely measured quantities of a drug at precisely planned intervals to give a gradual infusion of medication into the patient. The infusion pump makes possible a closer approximation to the natural maintenance of biochemical balances in the body because of its operation in a repetitive small dose mode.

Disposability is an important consideration in the design of medication infusion systems. Parts of the system through which medication is pumped must be sterile, so that in most applications some of the equipment is used and then discarded. The disposable parts are typically replaced at regular intervals, typically on a daily basis. Disposability of the fluid pump portion of the infusion device is a highly desirable feature. It would be very convenient to design a fluid pump in the form of an attachable cassette of economical design which could easily be installed onto a main pumping unit. A cassette which uses a small number of parts, is easily mass producible, and is capable of delivering liquid medication or other therapeutic fluids with a high degree of precision is described in U. S. Patent application Ser. No. 127,383, entitled "Disposable Cassette for a Medication Infusion System." The contents of that application are incorporated herein by reference.

The disposable cassette which is referred to above includes a fluid pump affording a high degree of accuracy in fluid delivery, with the degree of accuracy being maintained throughout the life of the product. The cassette also provides means for conveniently and easily priming the pump, and includes a bubble trap to prevent the frequent shutdowns and alarms which are a problem with presently available pumps. The cassette also includes additional devices such as pressure sensing means and bubble detecting means which in conventional medication infusion systems constitute separate assemblies.

A fluid monitoring and control system for use with disposable cassettes is needed to ensure accurate and safe delivery of therapeutic fluids. The design of such a system requires careful attention to factors involved in the accuracy of fluid delivery, and instrument monitoring functions are necessary to insure safe operation of the system.

There has been a long-felt but unresolved need for the development of a medication infusion management system that can be used for patient care in both hospitals and home health care applications. A desirable system would provide a reliable and improved product for current applications to encourage the use of new therapeutic techniques, reduce the cost of hospitalization by improving care and decreasing labor and inventory costs, and would be versatile enough to allow intra-arterial and subcutaneous infusions. Primary requirements of such a system would be volumetric accuracy, state-of-the-art safety functions, and a capacity for independently controlling more than one pumping channel, each with a separate line to the patient.

Ideally the pump of the improved medication infusion system would be substantially smaller and lighter than current hospital pumps while at the same time incorporating multiple pumping channels. Moreover, it is desirable to be able to configure selected system parameters and to monitor displayed information related to the needs and performance of a given system, thereby optimizing system operation. Together with the possibility of extended battery-powered operation, these features may be incorporated in a device that is particularly well suited to ambulatory care, intensive care, emergency transport, emergency care, or operating room use, as needed.

A system with the capacity for multiple pumping channels, a variety of disposable configurations, a maintenance mode, and a library of software functions could combine the capabilities of several currently available devices into one single unit. For example, the need in a hospital for separate syringe pumps, PCA pumps, neonatal pumps, general purpose pumps, and computer communications pumps could be eliminated in favor of one system that could satisfy the requirements for all these devices on a selective basis.

The capability of a medication infusion system to operate interchangeably on a selective basis in the emulation of the different types of pumps listed above would represent a significant cost savings for hospital administration with the elimination or substantial reduction of some of the costs associated with the use of medication infusion systems. A major reduction in inventory costs associated with infusion systems is possible if one pump apparatus can replace a plurality of different specific types. Also, the capability of a single medication infusion system to operate with a plurality of channels reduces equipment cost. Other cost benefits may result from a reduction in the number of different disposable peripherals which are required for the infusion system, a reduction in cost of required maintenance and an easing of personnel training requirements.

SUMMARY OF THE INVENTION

In brief, arrangements in accordance with the present invention provide for the clinical configuration of a multimode medication infusion system having the desirable characteristics listed above.

Various aspects of the multimode medication infusion system with which the present invention is associated are set forth in the co-pending patent applications which are identified on page 1 of this specification. The disclosures of those applications are incorporated herein by reference.

The clinical configuration concept of the present invention is particularly related to the user interface for the multimode medication infusion system which, briefly described, includes apparatus that is designed for use with a disposable fluid pathway that incorporates a sterile cassette containing pumping elements and sensor interfaces in a multi-channel configuration. The hardware portion of the user interface comprises an audio signal generator, status light-emittinq diodes (LEDs), a liquid crystal display (LCD), and user inputs. A programmed microprocessor allows the user to control the system through the user inputs. The audio signal generator is used to get the attention of the operator, the status LEDs allow the operator to make a quick visual check of the status of the instrument at a distance or in a darkened room, and the LCD presents all the detailed information about the system status and operation.

The user interface is designed to be a flexible mechanism to allow use of the system by relatively untrained personnel without sacrificing the capability for use by better trained personnel to control more complex infusion regimens which are possible with the system. Since the system has more than one pumping channel, the user interface allows simultaneous display of data pertaining to multiple infusion requirements. A variety of complex infusion regimens are possible on each pump, making the system potentially very complex, and for this reason the design of the user interface has been kept as simple and intuitive as possible.

While setting up an infusion regimen, the operator deals with only one pump at a time. When monitoring one or more regimens, the operator is able to view the most important information from each pump at a glance. Information is grouped in a clinically useful way and displayed on the LCD in specific formats referred to as "pages." Using the interface consists mainly of selecting the correct pages to view and, if necessary, changing information, responding to alarms, and so forth. The most significant information for each pump is displayed on the LCD in a format known as the "standard page." Basic infusion parameters such as infusion rate and volume remaining, as well as information about alarms and overall status can be viewed from this display. The standard page is the default display which appears initially without operator intervention.

The user interface imitates a single-pump infusion device for purposes of setting up an infusion regimen. Information relating to only one pump, the "selected" pump, is displayed at one time. The operator has the option of changing the "selected" pump at any time. The individual pump modes, or clinical device types, are established for the system by the setting of various parameters by qualified personnel, either at the factory by establishing fixed values of selected parameters or by qualified biomedical technicians at the hospital who determine the parameter values to be fixed as defaults. This latter default selection is referred to as an "instrument configuration," since it involves setting up the instrument in preparation for use at the clinical level.

Currently, different infusion devices are used in different areas of a hospital because of the specific needs of a particular area—intensive care units, operating room, neonatal and pediatric intensive care, to name a few examples. The different infusion devices have different infusion parameter ranges or settings (rate and volume remaining ranges, patient side occlusion and air-in-line alarm thresholds, etc.) They may also use different fluid containers (e.g., syringes, bottles, bags, etc.) and may have software for special applications (e.g., patient controlled analgesia, piggybacking, dosage calculation, etc.)

Specifically, hospitals currently use the following types of devices:

General Purpose—This type is used in intensive care units, the general floor, emergency rooms, labor and delivery. Its flow rate range is from 1 to 999 ml/hr; its alarm sensitivities are medium.

Neonatal—This type is used in neonatal and pediatric intensive care units. Its flow rate range is one-tenth that of the general purpose type (0.1 to 99.9 ml/hr); too high a rate can cause death. Its alarm sensitivity is established at the highest level.

Flow Controllers—These are used at the present time for cancer chemotherapy. They may also be used on the general floor. The flow rate range is from 1 to 299 ml/hr. As for alarms, occlusion pressure is the most sensitive of all, since it is determined by the fluid head height, which is low. This is important for infusing cancer chemotherapy drugs which can cause serious tissue damage during an infiltration.

Operating Room—The flow rate range is from 1 to 999 ml/hr (same as General purpose). Alarm sensitivity is defaulted to the lowest value, since an anesthesiologist is always present and numerous, particularly unnecessary, alarms are to be avoided since they may interrupt the flow of an important drug and may distract operating room personnel.

Home Health Care—Two flow rate ranges are provided: 0.1 to 99.9 ml/hr and 100 to 999 ml/hr. Alarm sensitivity is medium. Home health care units are usually battery powered.

In addition to the above-listed general device types, hospitals may purchase special devices because of the need for special functions, such as the delivery of fluids from a syringe, patient controlled analgesia (PCA) and piggybacking.

These various clinical device types and their respective parameter settings are set forth in Table I (below) which shows a comparison of the clinical device types to which the individual pump modes correspond and the different parameter values that are conventionally set at the factory as default settings. A given institution may have requested different default values from those shown in Table I in purchased equipment.

settings for those parameters which are not accessible to change at the clinician level.

BRIEF DESCRIPTION OF THE DRAWINGS

A better understanding of the present invention may be realized from a consideration of the following detailed description, taken in conjunction with the accompanying drawing in which.

DESCRIPTION OF THE PREFERRED EMBODIMENT

TABLE I

| PARAMETER | DEVICE TYPE | | | | |
|---|---|---|---|---|---|
| | GENERAL PURPOSE | CONTROLLER PRESSURE | OPERATING ROOM | NEONATAL | HOME HEALTH CARE |
| Occlusion Detection Method* | Baseline | Absolute Threshold | Baseline | Baseline | Baseline |
| Occlusion Alarm Setting | Baseline +5 psi | Absolute 3 feet | Baseline +10 psi | Baseline +1 psi | Baseline +5 psi |
| Air-in-Line Detector Sensitivity | 100 mcl | 100 mcl | 500 mcl | 50 mcl | 100 mcl |
| KVO rate ml/hr | 1.0 | 1.0 | 0.0 off | 0.1 | 1.0 |
| Rate Range ml/hr | 1–999 | 1–999 | 1–999 | 0.1–99.0 | 0.1–99.9 100–999 |
| Max. VR Setting (ml) | 9999 | 9999 | 9999 | 999.9 | 0.1–999.9 1000–9999.9 |
| Very low power mode* | no | no | no | no | yes |

*Settings which cannot be changed.

It will be noted that the settings for Occlusion Detection Method and very Low Power Mode cannot be changed. The baseline method or occlusion detection involves the pump channel recognizing a certain level of pressure when the infusion starts, and by overcoming that pressure to maintain fluid flow up to the specified increment above the baseline, at which point the occlusion alarm will sound. For example, a General Purpose Device set at baseline symbol +5 psi will alarm when it exceeds its baseline pressure by 5 psi.

Absolute threshold occlusion detection means that the occlusion pressure alarm is fixed at a certain value, and the pump channel will alarm whenever the occlusion pressure reaches that point. For example, a Controller Pressure Device will alarm at the equivalent of three feet of head height (pump to patient), regardless of the initial pressure required to overcome back pressure in the Iv line. The maximum pressure that the medication infusion system with which the present invention is associated is capable of is 15 psi, regardless of baseline pressure.

Figure 1:
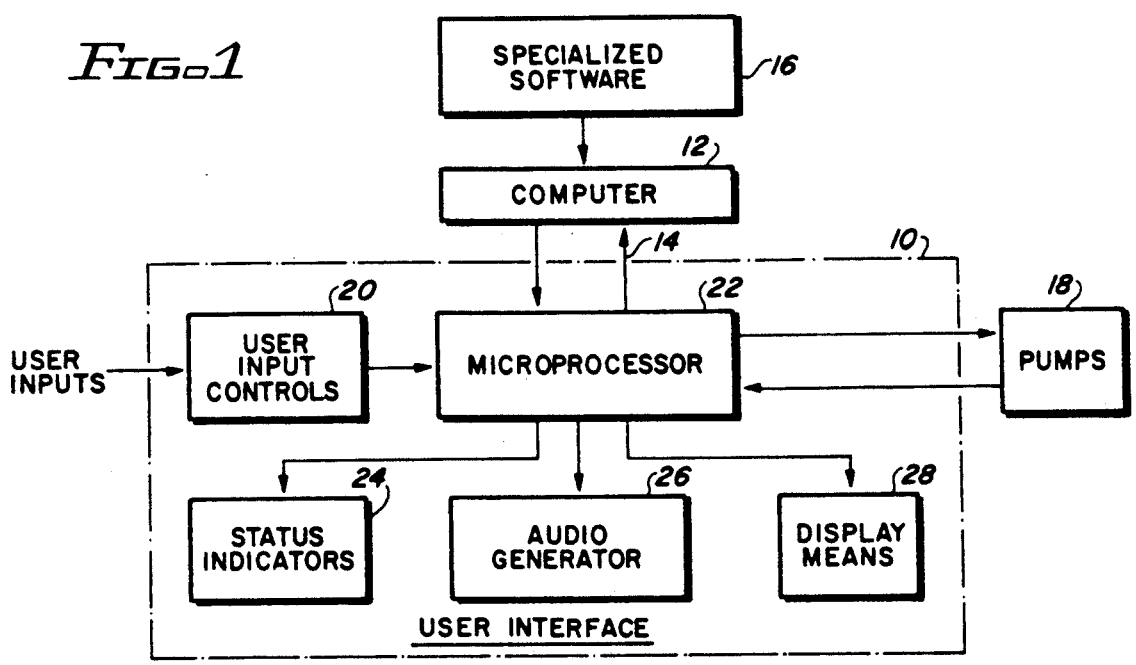
FIG. 1 is a schematic block diagram of the user interface in relation to a multimode medical infusion system.

In accordance with the present invention, the trained clinician can select a particular device type from among those shown on Table I based on the immediate need. With the present invention, the clinician can make certain limited choices with respect to the parameters for given device type and may visually check the default In accordance with the present invention, FIG. 1 is a schematic block diagram of a user interface for clinical configuration of a multimode medication infusion system as described in the related patent applications listed in "Identification of Related Patent Applications" above, which are hereby incorporated herein by reference. Referring to FIG. 1, user interface 10 is able to communicate with an off-line digital computer 12 via communications interface 14. When user interface 10 is connected to computer 12 in this way, specialized software 16 is run on computer 12 to enable selected qualified personnel to change default values for various parameters associated with operation of the medication infusion system. This mode of operation of user interface 10 is called the "instrument configuration mode."

Normally user interface 10 is not connected to computer 12. User interface 10 controls the functioning of a medication infusion system employing a disposable fluid pathway that incorporates a sterile cassette containing pumping elements 18 and sensor interfaces in a multi channel configuration, as described in U.S. Ser. No. 128,973, entitled "Fluid Delivery Control and Monitoring Apparatus for a Medication Infusion System," assigned to the assignee of this application.

User interface 10 comprises user input controls 20, a microprocessor 22, status indicators 24, an audio generator 26, and display means 28.

Figure 2:
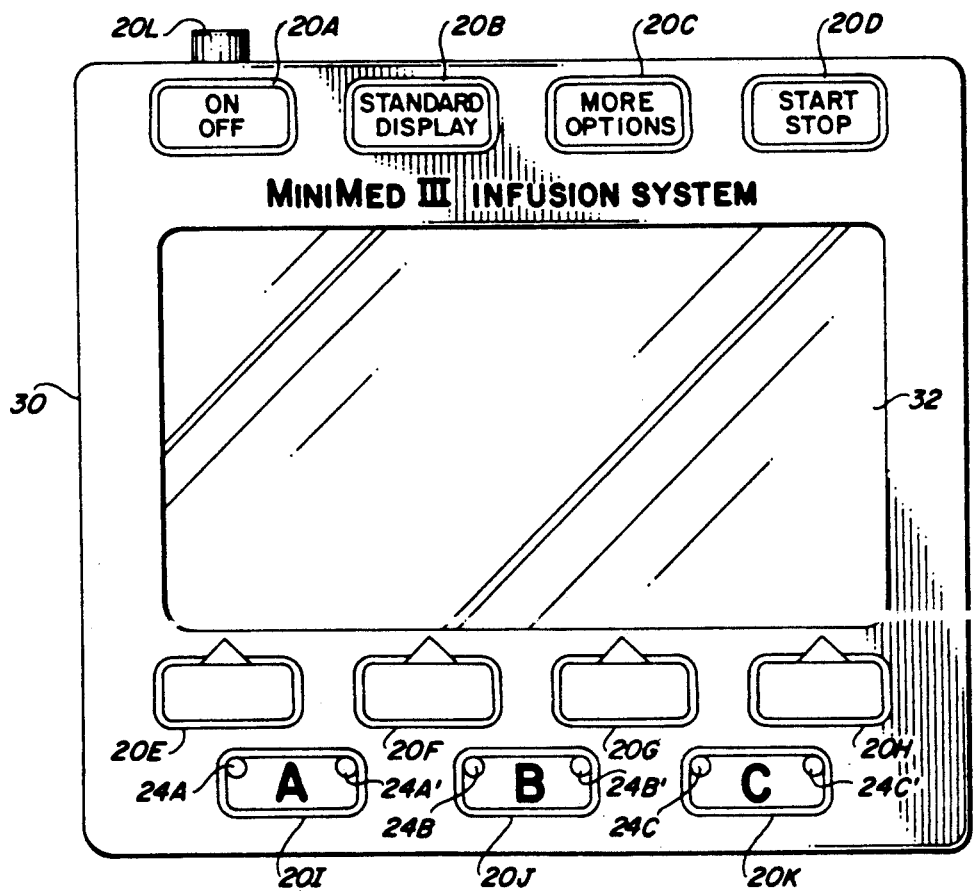
FIG. 2 is a front view of the user interface display device.

In a preferred embodiment the user interface 10 has four basic elements an audio signal generator, status light-emitting diodes (LEDs), a liquid crystal display (LCD), and a plurality of user inputs. FIG. 2 is a front view of user interface hardware in the preferred embodiment. A user interface chassis 30 houses a liquid crystal display 32, above which are four user input controls 20a-20d, and below which are user input controls 20e-20k.

Input controls 20a-20d are momentary-contact switches labelled "on/off," "standard display," "More Options," and "start/stop," respectively. Switches 20e-20h are so-called softkeys, whose functions depend on what is being displayed on the LCD 32. Switches 20i-20k are used to select a pump for infusion. Switch 20l (not shown) is a patient-controlled analgesia switch.

The face of each pump select switch contains two status LEDs. Thus, pump select switch 20i has status LEDs 24a and 24a', pump select switch 20j has status LEDs 24b and 24b', and pump select switch 20k has status LEDs 24c and 24c'. The status LEDs 24 allow the user to make a quick visual check of the status of the instrument from a distance or in a darkened room, and the LCD 32 presents all detailed information about instrument status and operation. The user inputs 20a-20k allow the operator to control instrument operation.

Normally a user wants to deal with only one pump at a time when setting up an infusion regimen. User interface 10 is designed to facilitate this by grouping information in a clinically useful way on LCD 32 in a specific format referred to as a "page." Many different types of pages are defined for the instrument. Reference is made to the co-pending application entitled "User Interface for Multimode Medication Infusion System" for specific details of the various pages which are available for display on the display device 32. However, details of the clinical configuration pages will be described hereinbelow.

Figure 3:
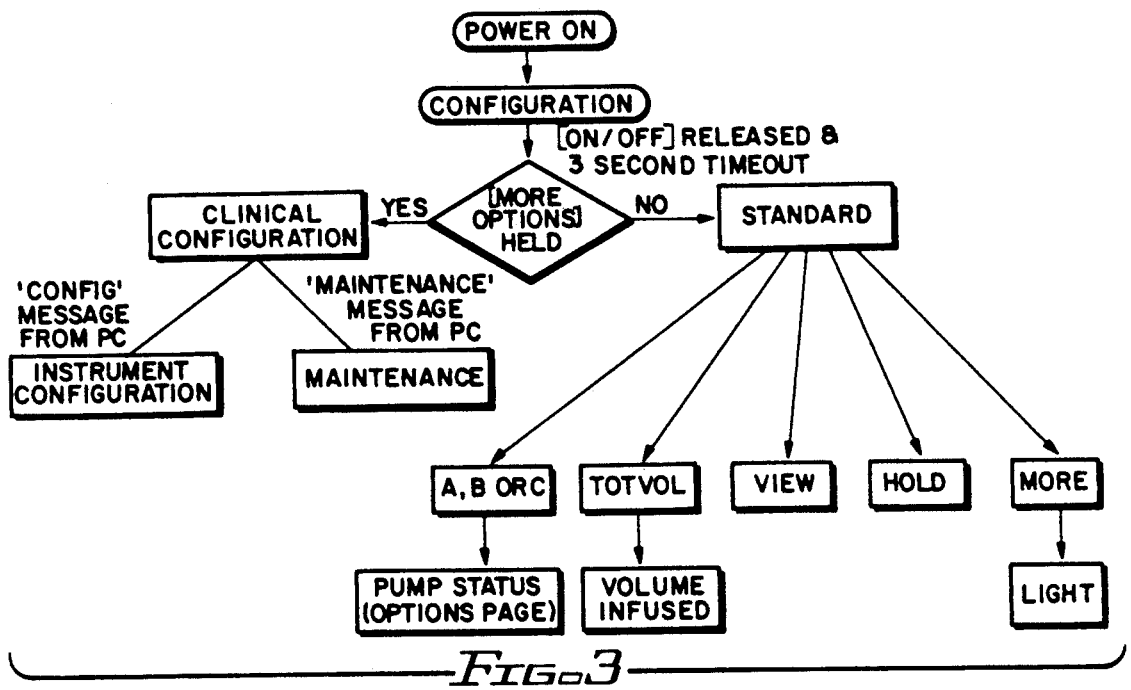
FIG. 3 is a schematic flow diagram of the overall structure of the user interface, a portion of which represents the clinical configuration feature of the present invention.

FIG. 3 indicates the overall operational structure of the user interface. Boxes with rounded corners denote liquid crystal display pages. The transitions from one LCD page to another are shown. The event which triggers a transition is shown in a rectangle superimposed on the transition (an operator activation of a control) or a label next to the transition (an instrument-triggered change). All transitions operate from top to bottom or left to right. For example, to move from the standard page to a pump status page, the operator activates a pump select key "A," "B," or "C."

Many pages have "More Options" softkey functions defined. Note that a "More Options" activation without any corresponding display change denotes that the primary set of softkey options is re-displayed. If no secondary sets of softkeys are defined, the "More Options" softkey has no effect.

All pages subordinate to the standard display have a transition to the standard display after 60 seconds of front panel keyboard inactivity. In addition, there is an implied transition from all LCD pages to the standard page, using the "standard display" key. An implied transition from all clinical operations display pages to a pump status page exists, by activation of the appropriate pump select key "A," "B," or "C."

Some boxes in FIG. 3 show more than one softkey function. Only one of the functions in a box is available at any time, depending on conditions not shown on the chart.

LCD 32 is used for all data entry and display for the system. Four types of information are presented:

(a) General status information for each pump;

(b) Prompts and other information to assist in setting up and using the pump;

(c) Sofkey labels; and (d) Detailed information about the instrument status and status for each of the pumps.

There are four clinical configuration pages which may be displayed individually on the LCD device 32. These are indicated in the left-hand side of FIG. 3 and are shown respectively in FIGS. 4-7. The relationship of Clinical Configuration to Instrument Configuration and Maintenance is described in detail in the co-pending application entitled "User Interface for Multimode Medication Infusion System," incorporated by reference herein.

Clinical configuration page 1 (FIG. 4) appears on the display when the operator uses the interface device to access the clinical configuration settings. The clinical configuration settings mode provides a special feature that allows the user to enter the time and date, to select the device type, to set the volume level of the audio alarm, and to review certain default settings.

Time And Date Settings

Figures 4, 5, 6, 7:
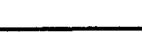
FIGS. 4–7 are a sequence of page displays in the clinical configuration mode of the present invention as they appear on the device of FIG. 2.

Page 1/ FIG. 4

The first page of the clinical configuration display shows the time, month, day and year. Each of these parameters can be changed by the clinician as needed. The time can also be displayed as am/pm or 24-hour military time.

Clinical Device Type

Page 2/FIG. 5

The Clinical Device Type affects all three pump channels. It is not possible to set different clinical device types for different pump channels; all three channels will always be the same device type, corresponding to a selected one of the available types shown in Table I above.

Audio Alarm Volume

Page 3/FIG. 6

The Audio Alarm Volume can be set to highest, high, medium, or low, and the setting determines the initial volume of the alarm tone. If an alarm is ignored, its volume will increase over time to the highest level.

Default Settings

Page 4/FIG. 7

This page (and any succeeding clinical configuration pages which may be needed for the purpose) shows the default settings for the Device Type to which the instrument has been preset. Changes to these settings are possible, but not at the clinician level. These changes can only be made with the use of specialized equipment by biomedical engineers using the instrument configuration mode, or by the manufacturer at the institution's request. Because it is recommended that any changes in the default settings be standardized throughout an institution, it is likely that all instruments used by the clinician will have the same default settings within each Device Type. The clinician can review the settings but cannot change them.

DESCRIPTION OF OPERATION

Supplying Power to the System

Power to the system is supplied by operator activation of the on/off switch. Pressing this control while the instrument is "off" supplies power to the electronics (assuming that the internal batteries are charged or an external power supply is attached) and causes an instrument reset. The instrument then:

(a) Performs a "power-on self test" (POST);
(b) Displays the current instrument configuration;
(c) Determines whether to operate in a non-clinical operating mode; and
(d) If clinical operation is entered, the standard page is displayed. Otherwise, the first clinical configuration page is displayed.

Details of clinical operation, including the initial display of the current configuration, the entry into clinical operation, pump selection, setup and review of infusion regimen, and the like may be found in co-pending application Ser. No. 128,978, entitled "User Interface for a Multimode Medication Infusion System."

Home-Health Care Instrument

When the pump is configured as a home-health care instrument certain functions of the instrument are altered to prevent accidental control activation and to maximize the operational life of the battery packs. The instrument operates in low-power mode. When the instrument is "on," the "on/off" and "start/stop" controls must be held down for one second before the instrument powers down or the infusion regimen starts or stops. A general feedback signal is given by the instrument. If the control is released in less than one second, the control activation is ignored.

Non-Clinical Operation

Because the instrument is capable of operating in a wide range or environments, performing extremely sophisticated functions, it is necessary to configure the operation of the instrument to the environment to which it is to be used. Without this configuration ability the user interface would become much more complicated. In addition, it is necessary to be able to test and maintain the operation of the instrument.

Configurability and maintenance functions must be performed when the instrument is not being used to infuse fluids into a patient Therefore, these functions are not available during normal operation and require special procedures in order to be accessed.

Configuration procedures are of two types: instrument configuration and clinical configuration. The basis for this division is the level of security required for the two configuration modes. Instrument configuration involves changing fairly sensitive information in the instrument, and is expected to be performed only in the biomedical engineering departments. The settings done in this mode are not to be changed by clinical personnel. Clinical configuration mode covers those parameters that may be changed by a knowledgeable clinical operator, based on the requirements of the patient and the environment. Maintenance functions should be confined to the biomedical engineering departments. To ensure that maintenance and instrument configuration functions are only performed outside of the clinical environment, these functions can be accessed only by using the communications capability of the instrument. The details of instrument configuration and maintenance may be found in application Ser. No. 128,978, entitled "User Interface for Multimode Infusion System," referenced above.

Clinical Configuration Pages

The clinical configuration page 1 is accessed by holding the "More Options" key before releasing the "on/off" control at instrument power on. This page displays a time display format which includes time, month, day, and year, as shown in FIG. 4. These settings may be entered or changed by using the Select softkey to choose the particular setting to be changed. Then the up or down arrow softkeys are used to change the value of the selected setting. Pressing the Accept softkey confirms the change, while the Recall softkey returns the setting to the old value. Each of the remaining settings on page 1 is selected and changed in the same manner. Page 2 displays the device type. Page 3 displays audio alarm volume. Page 4 displays the default values of the selected device type.

When the desired settings have been established on page 1, the clinician presses the STANDARD DISPLAY button to advance to page 2 (FIG. 5). This involves the selection of the Clinical Device Type. The clinician uses the Select softkey to select desired Clinical Device Type. Pressing the Accept softkey confirms the new Device Type. Pressing the Recall softkey returns to the old Device Type.

Depending on the institution's policy, it may not be possible to change the Clinical Device Type from the display of clinical configuration page 2. If the Clinical Device Type is locked out in the Instrument Configuration Mode, it is possible to review the Clinical Device Type but the type may not be changed through Clinical Configuration.

Changing the Device Type results in all previous infusion settings being cleared. Thus, after a change of Device Type, the clinical operation mode must be entered to establish proper infusion settings for that type of instrument.

Pressing the STANDARD DISPLAY button advances the display to clinical configuration page 3 (FIG. 6). This is the Audio Alarm volume page which permits setting the initial volume levels for the audio alarm. The up and down arrow softkeys are pressed to adjust the audio volume to the desired level. Thereafter, the Accept softkey is pressed to accept the new setting. Pressing RECALL returns the display to the old setting.

Pressing the STANDARD DISPLAY button from the display of page 3 advances the display to clinical configuration page 4 (FIG. 7). The settings which are displayed on clinical configuration page 4 can be reviewed but cannot be changed by the clinician. Pressing the STANDARD DISPLAY button from the page for display returns to clinical configuration page 1.

To exit the Clinical Configuration Mode, the apparatus must be turned off by pressing the ON/OFF button. When the apparatus is powered on again, all new Clinical Configuration Settings will be in effect. If the Device Type was changed, all previous infusion settings will have been cleared.

There have thus been disclosed the pertinent details of a particular aspect of a medication infusion system in accordance with the invention which permits the clinical user to configure the device for operation as any one of a plurality of device types which are preset for operation in different infusion system environments. Providing for operation of the system in this manner vastly simplifies the task of the clinician in setting up a medication infusion system for a particular selected use. Moreover, it improves the safety and efficiency of utilization of the system by eliminating the possibility of critical parameter settings being changed or improperly used by mistake, whether by the clinician or by unauthorized personnel who might have access to the system. At the same time, however, the clinical configuration mode of the present invention permits the clinical operator to view various parameter settings for the Device Type selected so that any erroneous parameter settings may be detected before the system is used. The main benefit of the present invention, however, is the assurance which is provided that selection of a particular Device Type automatically establishes the proper operating parameter settings for that type of device.

A secondary but still very important benefit resulting from the clinical configuration aspect of the present invention is the substantial economies which may be realized from the elimination of the hardware duplication of the different Device Types which are currently employed, required to be stocked in inventory, maintained, etc.

Although there have been described above specific arrangements of a clinical configuration of a medical infusion system in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A medication infusion system comprising:
   at least one infusion pump;
   means for selecting a group of parameter values from a plurality of parameter value groups, each of said plurality of parameter value groups characterizing a particular clinical mode for a medication infusion device;
   pump control means for controlling the operation of said infusion pump within the values of individual parameters contained in said selected group of parameter values;
   display means for displaying the different medication infusion devices characterized by said selected groups; and
   input means for selecting a particular one of the medication infusion devices displayed by said display means to be emulated by said infusion pump, said input means being functionally connected to operate said selecting means.

2. A medication infusion system as defined in claim 1, wherein said display means comprises a sequence of pages, and wherein said input means include means for selecting a particular one of said pages for viewing on said display means and means for changing information displayed on the selected page.

3. A medication infusion system as defined in claim 2, wherein the information displayed on the selected page comprises time and date information, and the input includes means for setting the time and date displayed on the selected page.

4. A medication infusion system as defined in claim 2, wherein the information displayed on the selected page comprises names of a plurality of medication infusion device types, and wherein the input means include means for designating a particular medication infusion device type on said page to be selected for emulation.

5. A medication infusion system as defined in claim 4, wherein the information displayed on a selected page comprises a first setable parameter for the infusion system and wherein the input means includes means for changing said setable parameter to correspond to a selected value for the particular medication infusion device type which is selected for emulation.

6. A medication infusion system as defined in claim 5, wherein said setable parameter comprises an alarm volume level and said input means includes means for setting said volume level to determine initial alarm sensitivity of the system.

7. A medication infusion system as defined in claim 4, wherein the information displayed on a selected page comprises parameter values for a selected medication infusion device type which the input means is incapable of changing, said input means including means for viewing the respective parameter types displayed on said page to check the correctness thereof.

8. A medication infusion system as defined in claim 4, wherein the medication infusion device types which are selected from emulation comprise: General Purpose, Neonatal, Flow Controller, Operating Room, and Home Health Care.

9. A medication infusion system as defined in claim 1, including a plurality of infusion pumps, all of said infusion pumps being controlled to emulate the particular medication infusion device type selected by said input means.

10. A medication infusion system as defined in claim 1, wherein said parameter values each comprise a range, a value, or an option.

11. A medication infusion system configurable for operation in multiple medication infusion applications, comprising:
    a first infusion pump;
    first controlling means for controlling the operation of said first infusion pump within a plurality of operational parameters;
    means for displaying a list of specific medication infusion applications in which said system is configurable;
    means for storing a plurality of groups of operational parameters, each group of operational parameters containing a plurality of operational parameters, each of said groups of operational parameters being associated with operation of said system in one of the specific medication infusion applications in said list; and
    means for selecting a particular one of said specific medication infusion applications in said list and for supplying the operational parameters in the group of operational parameters associated with said operation of said system in the selected specific medication infusion application from said storing means to said first controlling means, said first controlling means thereby controlling the operation of said first infusion pump within he operational parameters in the group of operational parameters associated with said operation of said system in the selected specific medication infusion application.

12. A medication infusion system as defined in claim 11, additionally comprising:
a second infusion pump; and
a second controlling means for controlling the operation of said second infusion pump within a plurality of operational parameters, said second controlling means thereby controlling the operation of said second infusion pump within the operational parameters in the group of operational parameters associated with said operation of said system in the selected specific medication infusion application.

13. A medication infusion system as defined in claim 12, additionally comprising:
a third infusion pump; and
a third controlling means for controlling the operation of said third infusion pump within a plurality of operational parameters, said third controlling means thereby controlling the operation of said third infusion pump within the operational parameters in the group of operational parameters associated with said operation of said system in the selected specific medication infusion application.

14. A medication infusion system as defined in claim 11, wherein said operational parameters each comprise:
a ranges, a value, or an option.

15. A medication infusion system as defined in claim 14, wherein said operational parameters comprise:
a range for the rate at which fluid may be pumped by said first infusion pump; and
a range for the volume of fluid which may be pumped by said first infusion pump.

16. A medication infusion system as defined in claim 15, additionally comprising:
means for inputting a specific infusion rate within said range for the rate at which fluid may be pumped by said first infusion pump; and
means for inputting a specific infusion volume to be infused within said range for the volume of fluid which may be pumped by said first infusion pump.

17. A medication infusion system as defined in claim 14, wherein said operational parameters comprise:
an occlusion detection option selected from the group including the Baseline method and the Absolute method.

18. A medication infusion system as defined in claim 17, wherein said operational parameters comprise:
an occlusion pressure value beyond which an alarm will be sounded.

19. A medication infusion system as defined in claim 14, wherein said operational parameters comprise:
an air-in-line detector sensitivity value.

20. A medication infusion system as defined in claim 14, wherein said operational parameters comprise: p1 a keep-vein-open infusion rate value.

21. A medication infusion system as defined in claim 14, wherein said operational parameters comprise:
a low power mode option.

22. A medication infusion system as defined in claim 11, wherein said specific medication infusion applications comprises:
a general purpose infusion pump application;
a neonatal infusion pump application;
a controller pressure infusion pump application; and
an operating room infusion pump application.

23. A medication infusion system as defined in claim 22, wherein said specific medication infusion applications additionally comprise:
a home health care infusion pump application.

24. A medication infusion system as defined in claim 22, wherein said specific medication infusion applications additionally comprise:
a second general purpose infusion pump application having operational parameters varying at least in part from the parameters of said general purpose infusion pump.

25. A medication infusion system as defined in claim 22, wherein said specific medication infusion applications additionally comprise:
a second operating room infusion pump application having operational parameters varying at least in part from the parameters of said operating room infusion pump.

26. A medication infusion system as defined in claim 22, wherein said specific medication infusion applications additionally comprise:
an insulin infusion pump application.

27. A medication infusion system as defined in claim 11, additionally comprising:
means for changing the value of said operational parameters.

28. A medication infusion system configurable for operation in multiple medication infusion applications, comprising:
at least one infusion pump;
means for controlling the operation of said infusion pump within a plurality of operational parameters, said operational parameters each comprising a ranges, a value, or an option;
means for displaying a list of specific medication infusion applications in which said system is configurable;
means for storing a plurality of groups of operational parameters, each group of operational parameters containing a plurality of operational parameters, each of said groups of operational parameters being associated with operation of said system in one of the specific medication infusion applications in said list;
means for selecting a particular one of said specific medication infusion applications in said list and for supplying the operational parameters in the group of operational parameters associated with said operation of said system in the selected specific medication infusion application from said storing means to said controlling means, said controlling means thereby controlling the operation of said infusion pump within the operational parameters in the group of operational parameters associated with said operation of said system in the selected specific medication infusion application; and
means for inputting a specific value for each operational parameter comprising a range.

29. A medication infusion system configurable for operation in multiple applications, comprising:
at least one infusion pump;
means for controlling the operation of said infusion pump within a plurality of operational parameters;
means for displaying a list of specific applications in which said system is configurable;
means for storing a plurality of groups of operational parameters, each group of operational parameters containing a plurality of operational parameters, each of said groups of operational parameters being associated with operation of said system in one of the specific applications in said list; and means for selecting a particular one of said specific applications in said list and for supplying the operational parameters in the group of operational parameters associated with said operation of said system in the selected specific application from said storing means to said controlling means.

30. A method of configuring a medication infusion system for operation in multiple medication infusion applications, comprising:

controlling the operation of at least one infusion pump within a plurality of operational parameters;

displaying a list of specific medication infusion applications in which said system is configurable;

storing a plurality of groups of operational parameters, each group of operational parameters containing a plurality of operational parameters, each of said groups of operational parameters being associated with operation of said system in one of the specific medication infusion applications in said list; and selecting a particular one of said specific medication infusion applications in said list and supplying the operational parameters in the pump of operational parameters associated with said operation of said system in the selected specific medication infusion application from said storing means to said controlling means, said controlling means thereby controlling the operation of said infusion pump within the operational parameters in the group of operational parameters associated with said operation of said system in the selected specific medication infusion application.

* * * * *

UNITED STATES PATENT AND TRADEMARK OFFICE
CERTIFICATE OF CORRECTION

PATENT NO. : 5,041,086
DATED : August 20, 1991
INVENTOR(S) : Paul A. Koenig, John B. Slate, O. Rey Rule, III, Fredric C. Colman It is certified that error appears in the above-identified patent and that said Letters Patent is hereby corrected as shown below:

Column 1, line 9, change "127,33" to --127,333--.

Column 1, line 22, change "128,133" to --128,973--.

Column 2, line 24, change "127,383" to --127,333--.

Column 13, line 57, after "comprise :" delete the expression "p1".

Signed and Sealed this

Thirtieth Day of July, 1996

Attest:

BRUCE LEHMAN

*Attesting Officer*  *Commissioner of Patents and Trademarks*